United States Patent
Wolanske et al.

(10) Patent No.: US 11,246,733 B2
(45) Date of Patent: Feb. 15, 2022

(54) RECOIL AND SPINAL ARMOR SUPPORT SYSTEM

(71) Applicant: Walter J. Wolanske, Cheektowaga, NY (US)

(72) Inventors: Walter J. Wolanske, Cheektowaga, NY (US); Samuel Morris, III, Buffalo, NY (US); Michael Schuler, Hamburg, NY (US)

(73) Assignee: Walter J. Wolanske, Cheektowaga, NY (US)

( * ) Notice: Subject to any disclaimer, the term of this patent is extended or adjusted under 35 U.S.C. 154(b) by 517 days.

(21) Appl. No.: 15/975,967

(22) Filed: May 10, 2018

(65) Prior Publication Data

US 2019/0343673 A1    Nov. 14, 2019

(51) Int. Cl.
*A61F 5/02* (2006.01)

(52) U.S. Cl.
CPC .............. *A61F 5/028* (2013.01); *A61F 5/024* (2013.01)

(58) Field of Classification Search
CPC .. A61F 5/028; A61F 5/024; A61F 5/02; A61F 5/026; A61F 5/022; A41D 13/0525; A41D 13/0531; A41D 13/05
USPC ........... 602/19, 5, 63, 62, 6; 128/96.1, 100.1
See application file for complete search history.

(56) References Cited

U.S. PATENT DOCUMENTS

| | | | |
|---|---|---|---|
| 6,213,968 B1 | 4/2001 | Heinz | |
| 6,610,022 B1 | 8/2003 | Ashbaugh | |
| 6,666,838 B2 | 12/2003 | Modglin | |
| 6,964,644 B1 * | 11/2005 | Garth | A61F 5/028 128/876 |
| 7,001,348 B2 | 2/2006 | Garth | |
| 7,449,006 B2 | 11/2008 | Wolanske | |
| 2002/0068890 A1 * | 6/2002 | Schwenn | A61F 5/0193 602/19 |
| 2010/0168630 A1 * | 7/2010 | Cropper | A61F 5/30 602/19 |
| 2010/0217167 A1 * | 8/2010 | Ingimundarson | A61F 5/028 602/19 |

* cited by examiner

*Primary Examiner* — Alireza Nia
*Assistant Examiner* — Robin Han
(74) *Attorney, Agent, or Firm* — Roach, Brown, McCarthy & Gruber, P.C.; Kevin D. McCarthy

(57) ABSTRACT

A back support system adapted to be worn by a person, has (a) a pivot adjusting balance member system, (b) a flexible spine aligner, or (c) combination thereof.

19 Claims, 10 Drawing Sheets

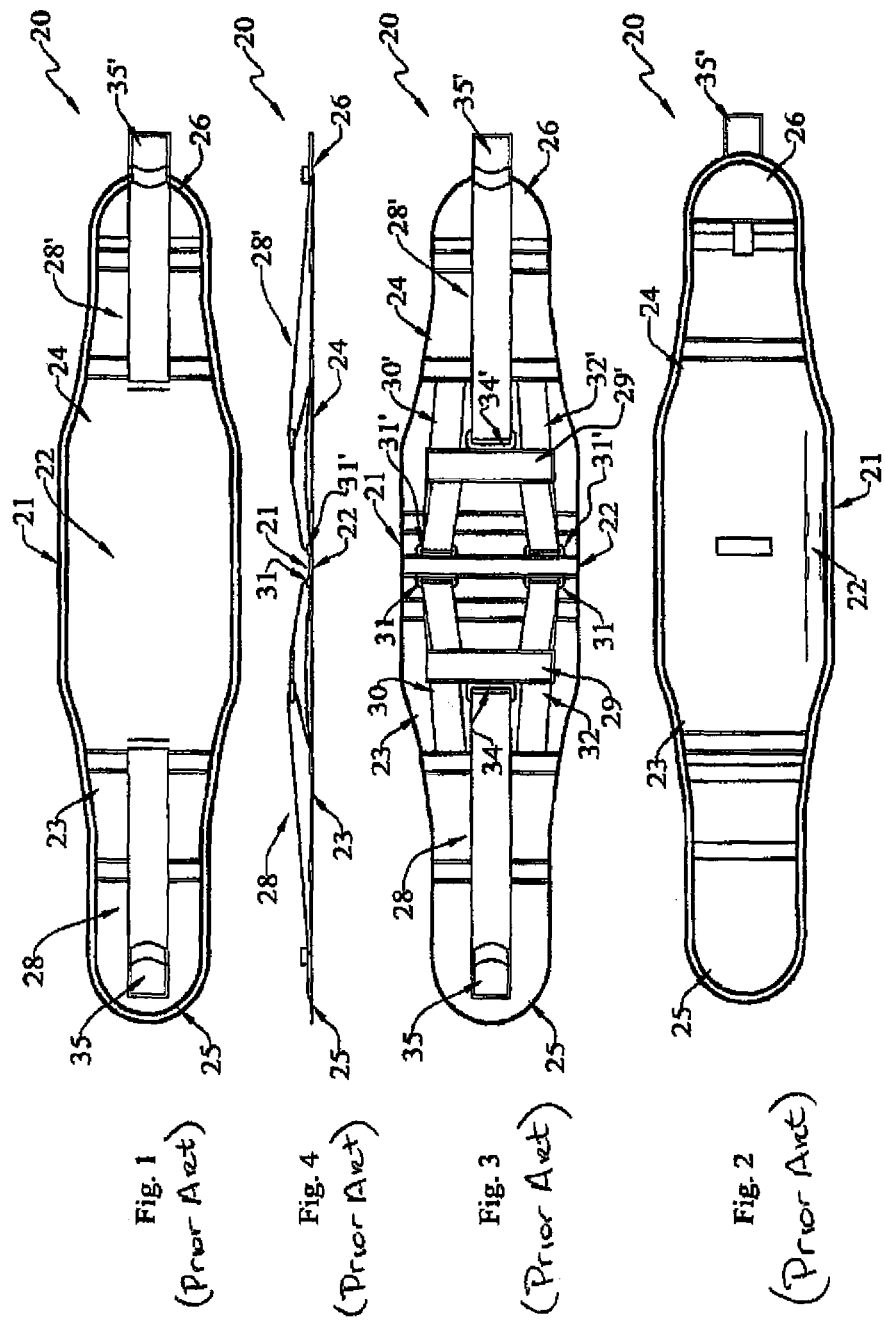

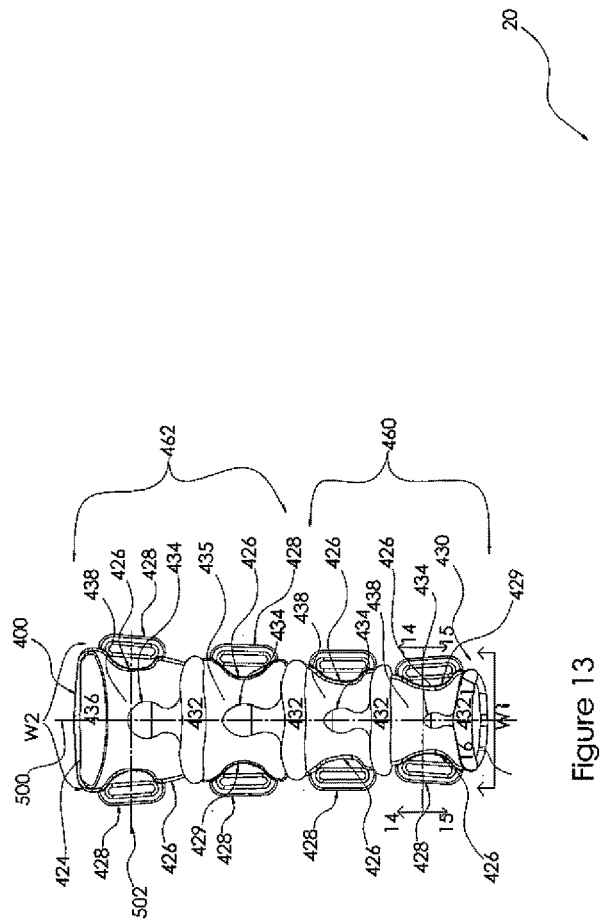

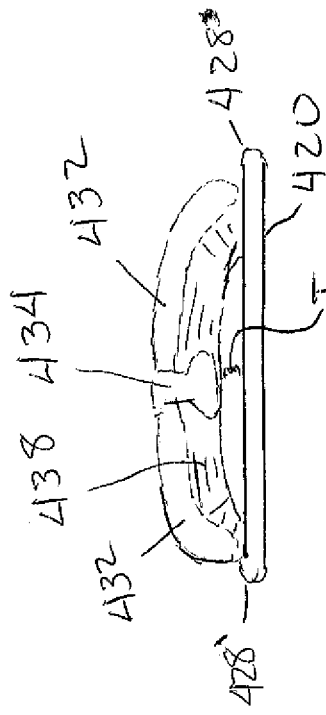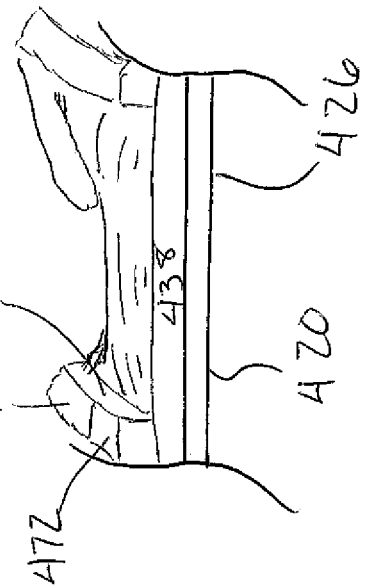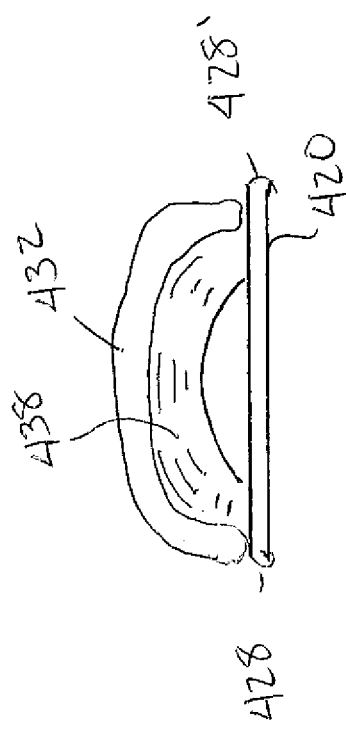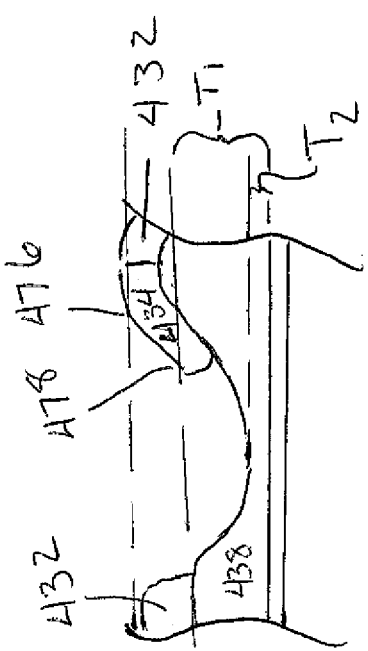

RECOIL AND SPINAL ARMOR SUPPORT SYSTEM

TECHNICAL FIELD

The present invention relates generally to the field of back support systems and lumbar orthotic devices, and, more particularly, to an improved back support system that can be quickly and easily tightened, loosened and adjusted, and that automatically equalizes the forces exerted on the upper and lower portion of the support system independently of whether the wearer is standing or sitting.

BACKGROUND ART

Many people suffer from back pain. There are many possible causes of this pain. In some cases, the pain may be reduced or alleviated by a suitable brace or support. Back braces are certainly known.

One such brace is shown in U.S. Pat. No. 7,001,348. This reference discloses an adjustable back brace with a rear portion, two side portions, and overlapable marginal end portions. Two pull tabs are adjustably mounted on each of the side portions, and are used to selectively tighten upper and lower cords at the rear of the brace. The pull tabs may be operated separately to adjust the cords independently of one another. Thus, it is possible for the upper portion of the brace to be tightened more than the lower portion, and this is further complicated when the wearer stands or sits.

Other details of braces are shown and described in U.S. Pat. Nos. 6,666,838, 6,610,022, 6,213,968 and 6,964,644. Applicant also discloses a back brace in U.S. Pat. No. 7,449,006, which discloses the following:

Referring now to the prior art drawings to FIGS. 1-4 thereof, the [back brace] broadly provides a self-adjusting and self-equalizing back brace, of which is generally indicated at 20.

Brace 20 is adapted to be worn by a person (not shown). The brace is shown as including a closable band 21 adapted to encircle a wearer's torso. The band has a rear portion 22 adapted to be positioned proximate the spine of a wearer, and has lateral side portions 23, 24 extending leftwardly and rightwardly, respectively, away from the back portion 21. These side portions terminate in left and right marginal end portions 25, 26, respectively, that are adapted to overlap one another in front of a wearer. These overlapped marginal end portions may be provided with various hook-and-loop fasteners, to secure the band about the torso of a wearer. Other types of fastening devices might be substituted for such hook-and-loop fasteners. Rear portion 22 may be formed of an elastic material that will not gather, if desired.

In the illustrated embodiment, the form is shown as having two tightening mechanisms. The left tightening mechanism is generally indicated at 28, and the right tightening mechanism is generally indicated at 28'. Inasmuch as these two tightening mechanisms are substantially identical, and are arranged as mirror images of one another, only the left tightening mechanism will be explicitly described. The reader will understand that the prime and same reference numeral will refer to the corresponding parts, portions or structure of right tightening mechanism 28'.

Left tightening mechanism 28 is shown as including an intermediately-pivoted member 29. An upper trace 30 in the form of a flexible tape, has its left marginal end portion anchored, as by stitching, to an intermediate portion of the left side, has an intermediate portion passed through an eyelet 31 secured to the rear portion 22, and has its other marginal end portion suitably affixed to the upper marginal portion of intermediately-pivoted member 29. Tightening mechanism 28 also includes a lower trace 32 having its left marginal end secured to a lower portion of the band, having an intermediate portion passed through another eyelet 33 attached to the rear portion, and having its other marginal end portion secured to the lower marginal end of intermediately-pivoted member 29. Member 30 also has another eyelet 34 that is positioned on the opposite side of member 29 substantially equally between the points of affixation of the upper and lower traces. A pull strip, generally indicated at 35, has one end secured to the band, has an intermediate portion passed through eyelet 34, and has another marginal end portion adapted to overlay the left band. The facing surfaces of the left band and the pull strip may be provided with a suitable hook-and-loop fasteners such that the wearer need only grab the distal end of the pull strip, and pull it leftwardly, to selectively tighten the brace about his torso, and then reattach it to the band. The back and/or side panels may contain a pocket, such as indicated at 40, into which a stiffening insert 41 may be received.

As noted above, in the illustrated embodiment, there are two such tightening mechanisms. The left tightening mechanism 28 is shown as being operatively associated with the left side portion of the band, and the right tightening mechanism 28' is operatively associated with the right side portion of the band.

The upper and lower traces are of substantially equal length, the operator need only pull on one or both of the pull strips to tighten the brace about his torso. Such eyelet 34 is located proximate the midpoint of the points at which the upper and lower traces are attached to the intermediately-pivoted member, such tightening of pull strip 35 will cause the tensile forces in the upper and lower traces to be substantially equal to one another. Moreover, the device is somewhat self adjusting in that the intermediately-pivoted member will move or flex appropriately, as the patient stands or sits. The salient feature here is that regardless of the position of the wearer's torso, a tightening of the appropriate tightening mechanism will exert substantially equal forces on the upper and lower traces. Thus, the device is self-equalizing and self-adjusting.

As indicated above, in the preferred embodiment, there are two separate tightening mechanism, one on the left side portion, and the other on the right side portion. These tightening mechanisms may be operated independently or together to affect the desired degree of tightening.

The aggregate disclosures of each of the above-cited patents are hereby incorporated by reference.

The above-identified back braces have been improved with the current embodiment of the present inventions.

DISCLOSURE OF THE INVENTION

The present invention broadly provides an improved back support system that is adapted to be worn by a person (not shown).

The back support system adapted to be worn by a person, has (a) a pivot adjusting balance member system, (b) a flexible spine aligner, or (c) combination thereof.

The pivot adjusting balance system has a proximal pivot support and a distal pivot support. The proximal support has an upper eyelet and a lower eyelet on its proximal end, a first pivot aperture, an upper extension with an upper pivot, downwardly curvilinear guide aperture, a lower extension with a lower pivot, upwardly curvilinear guide aperture, and a pull strap space positioned (a) between the upper extension and the lower extension and (b) distally spaced from the pivot aperture. The distal pivot support has a second pivot aperture, an upper pivot aperture, a lower pivot aperture, a pull strap aperture, at least one flexible aperture, and a pull strap retainer. The first pivot aperture aligns with the second pivot aperture, the upper pivot, downwardly curvilinear guide aperture aligns with the upper pivot aperture and the lower pivot, upwardly curvilinear guide aperture aligns with the lower pivot aperture. A first fastener secures the first pivot aperture to the second pivot aperture, a second fastener secures the upper pivot, downwardly curvilinear guide aperture to the upper pivot aperture, and a third fastener secures the lower pivot, upwardly curvilinear guide aperture to the lower pivot aperture.

The flexible spine aligner has (a) a planar support interior surface adapted to contact the band, (b) a superior end having a first width, (c) an inferior end having a second width which is greater than the first width, (d) a centerline that extends from the superior end to the inferior end of the flexible spine aligner, (e) a left side, (f) a right side, (g) a plurality of eyelet pair sets, each eyelet pair set has a first eyelet extending outwardly from the left side and a second eyelet extending outwardly from the right side, (h) a flexible section of a vertebral arch configuration exterior surface contains one eyelet pair set, each flexible section has a convex polymeric surface between the right and left sides, a concave polymeric surface that extends from the flexible section's superior end to the flexible section's interior end, and along the centerline, the two highest points relative to the planar support interior surface in each flexible section are at the superior end and interior end.

Accordingly, the general object of the invention is to provide an improved back support system.

Another object is to provide an improved back support system that is automatically self-adjusting and force-equalizing in the sense that the upper and lower portions will be placed under equal tensile loads by the simple action of a pulling a pull strip.

Still another object is to provide an improved back support system that will self-adjust to exert substantially equal forces on the upper and lower portions independently of the position of the wearer's torso (i.e., whether standing or sitting).

These and other objects and advantages will become apparent from the foregoing and ongoing written specification, the drawings, and the appended claims.

BRIEF DESCRIPTION OF THE DRAWINGS

FIG. 1 is prior art and a rear elevational view looking at the exterior surface of the improved back support system, in an extended, flat condition, this view showing the left and right pull strips as issuing from slits provided in the rear cover.

FIG. 2 is prior art and a front elevational view looking at the interior surface of the support system shown in FIG. 1.

FIG. 3 is prior art and a schematic interior view of the support system shown in FIGS. 1 and 2, with the rear cover removed and showing the two tightening mechanisms, and the various members and traces associated therewith.

FIG. 4 is prior art and a top plan view of the support system shown in FIG. 3.

FIG. 8 is view of FIG. 6 taken along the lines 8-8.

FIG. 12 is a side view of a spinal armor embodiment.

FIG. 13 is a top view of the flexible spinal spine aligner of FIG. 12 taken along the lines 13-13.

FIG. 14 is a cross-sectional view of FIG. 13 taken along the lines 14-14.

FIG. 15 is a cross-sectional view of FIG. 13 taken along the lines 13-13.

FIG. 16 is a cross-sectional view of FIG. 13 taken along the lines 16-16.

FIG. 17 is a cross sectional view of FIG. 13 taken along the lines 17-17.

DESCRIPTION OF THE PREFERRED EMBODIMENTS

Figure 5:
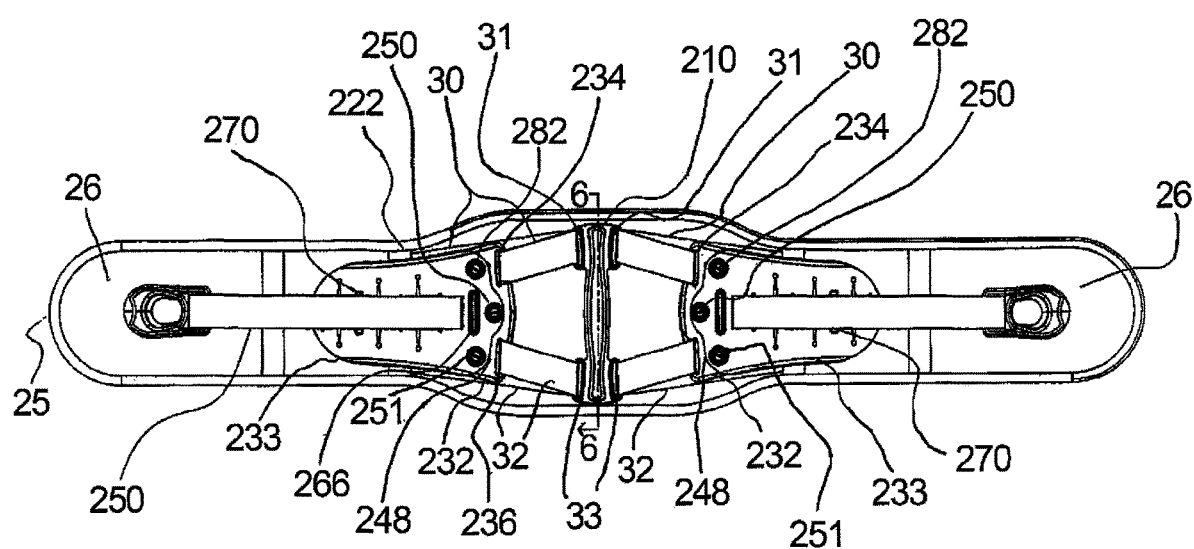
FIG. 5 is a rear elevational view of a recoil support system embodiment without a rear cover.

Applicant admits some components identified at U.S. Pat. No. 7,449,006, see background section of this application, are also incorporated and used in the current inventions. Accordingly, those components that are identical will use the same numbers as identified in U.S. Pat. No. 7,449,006.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Recoil Embodiment

As illustrated at FIG. 5, support system 20 is adapted to be worn by a person (not shown). The support system 20 is shown as including a closable band 21 adapted to encircle a wearer's torso. The band has a spine aligner 210 adapted to be positioned proximate the spine of a wearer, a rear portion 22 (see FIG. 11), a base portion 290 (see FIG. 5) wherein the spine aligner is permanently attached or removably attached, for example, hook and loop fasteners or equivalents thereof, to the base portion 290, and has lateral side portions 23, 24 extending leftwardly and rightwardly, respectively, away from the rear portion 22. Positioned at or near the intersection between the rear portion 22 and (a) the lateral side portion 23 is a tension portion 222; and (b) the lateral side portion 24 is a tension portion 222'. Tension portions 222, 222' are, respectively, anchors for pull straps 250, 250', and traces 30, 30', 32, 32'.

Figure 11:
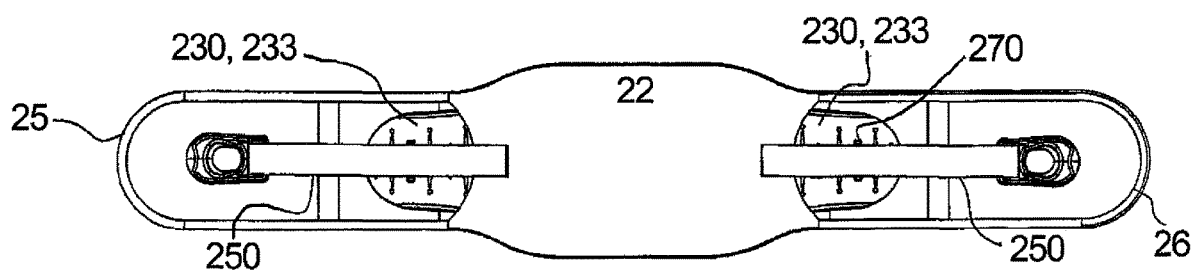
FIG. 11 is FIG. 5 with a rear portion thereon.

Those side portions 23, 24, respectively, terminate in left and right marginal end portions 25, 26 and the marginal end portions 25, 26 are adapted to overlap one another in front of a wearer. These overlapped marginal end portions may be provided with various hook-and-loop fasteners, to secure the band about the torso of a wearer. Other types of fastening devices might be substituted for such hook-and-loop fasteners. Rear portion 22 (see FIG. 11) and base portion 290 (see FIG. 5) may be formed of an elastic material that will not gather, if desired. That elastic material may be an elastic polyurethane fabric, like Lycra™ brand fabric, and it has been determined that stretching the elastic material toward the marginal end portions permits center balance member systems 230, 230' to a reset position, as illustrated at FIGS. 5 and 11.

In the illustrated embodiment, the form is shown as having two center balance member systems (sometimes referred to as equalizers) 230, 230'. The left center balance member system is generally indicated at 230, and the right center balance member system is generally indicated at 230'. Inasmuch as these two center balance member system 230 are substantially identical, and are arranged as mirror images of one another, only the left center balance member system 230 will be explicitly described. The reader will understand that the prime and same reference numeral will refer to the corresponding parts, portions or structure of right center balance member system 230'.

Figure 6:
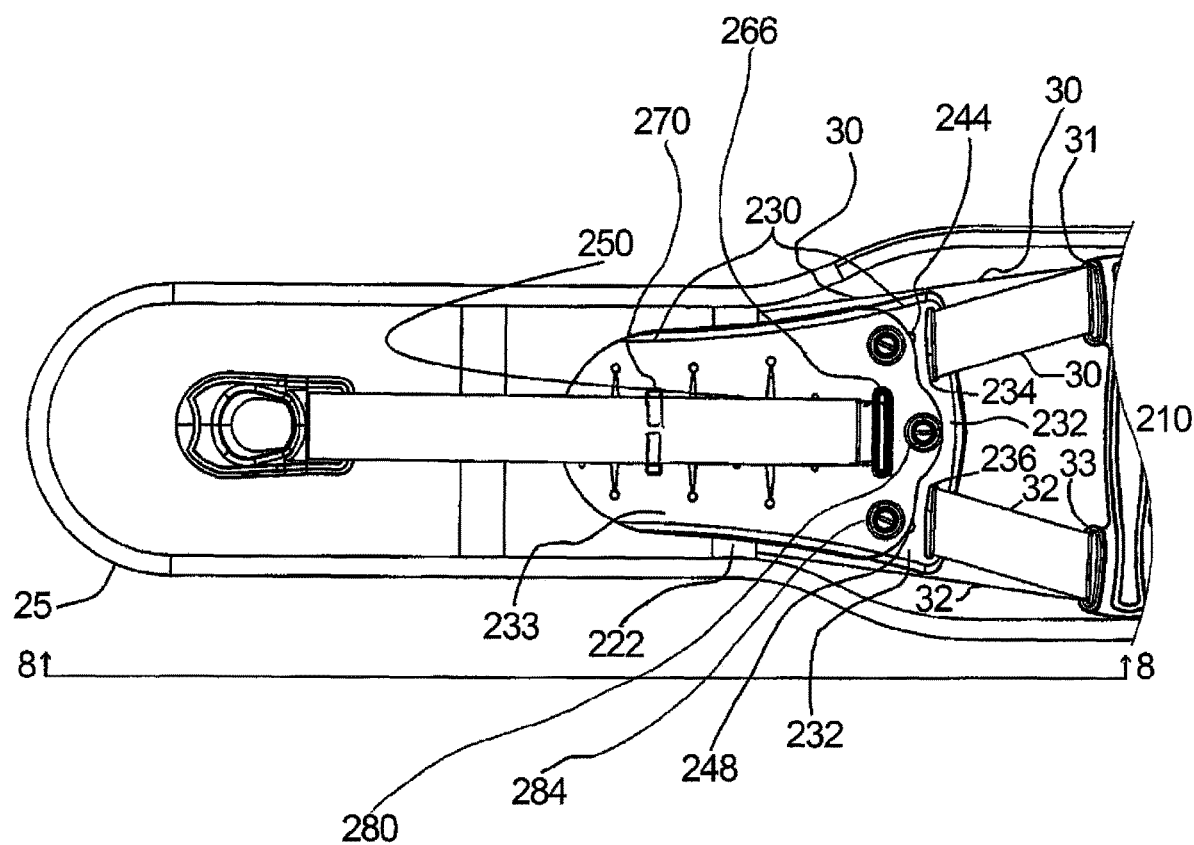
FIG. 6 is an enlarged view of FIG. 5 taken of box 6.
Figure 7:
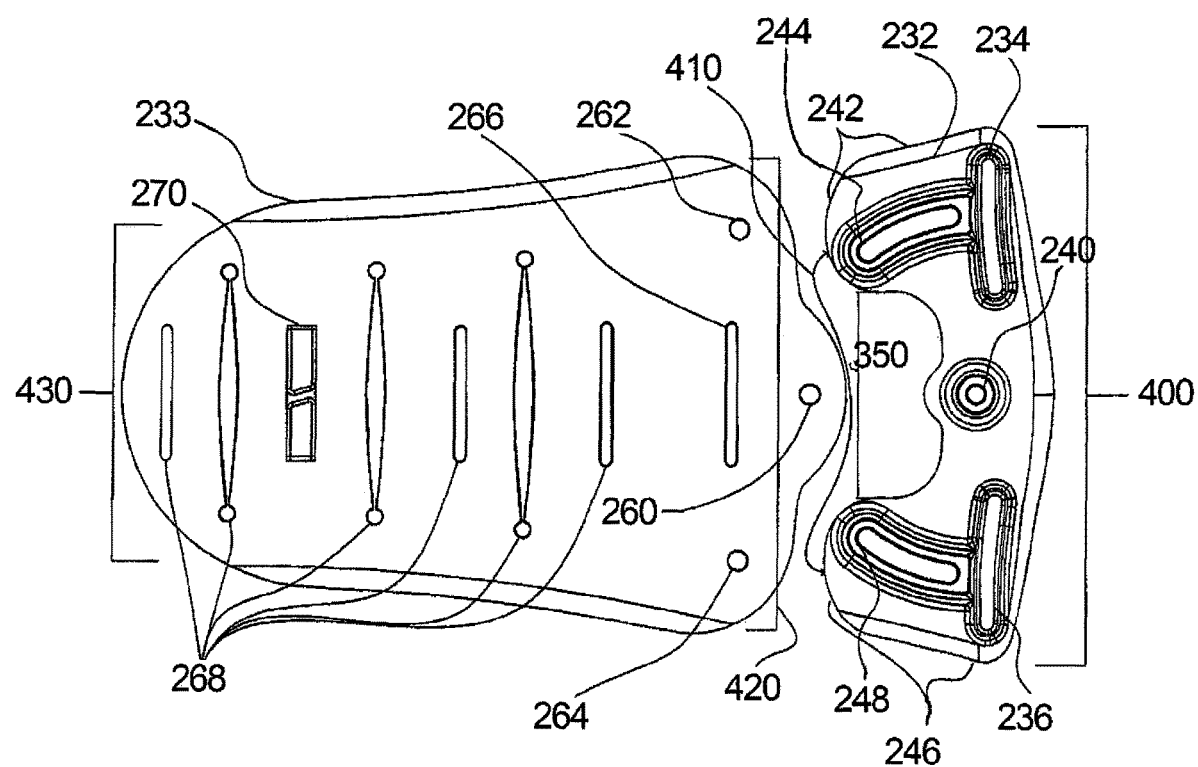
FIG. 7 is an exploded view of a center balance member system's proximal pivot support and distal pivot support.
Figure 6:
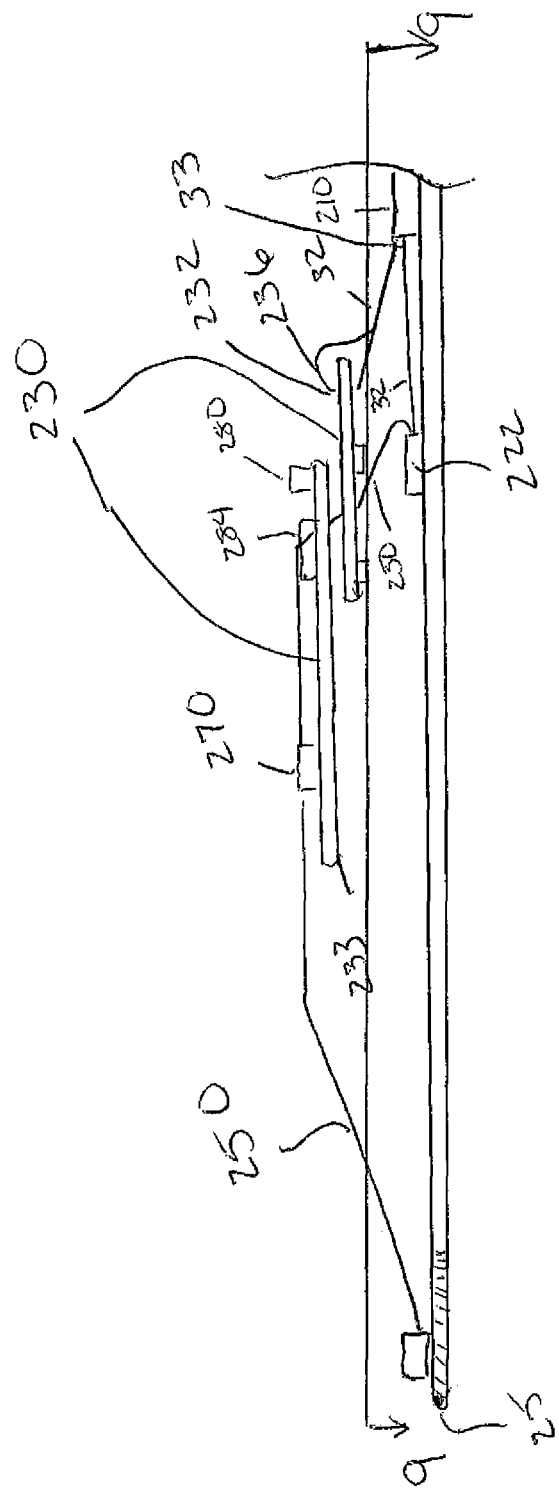
Figure 9:
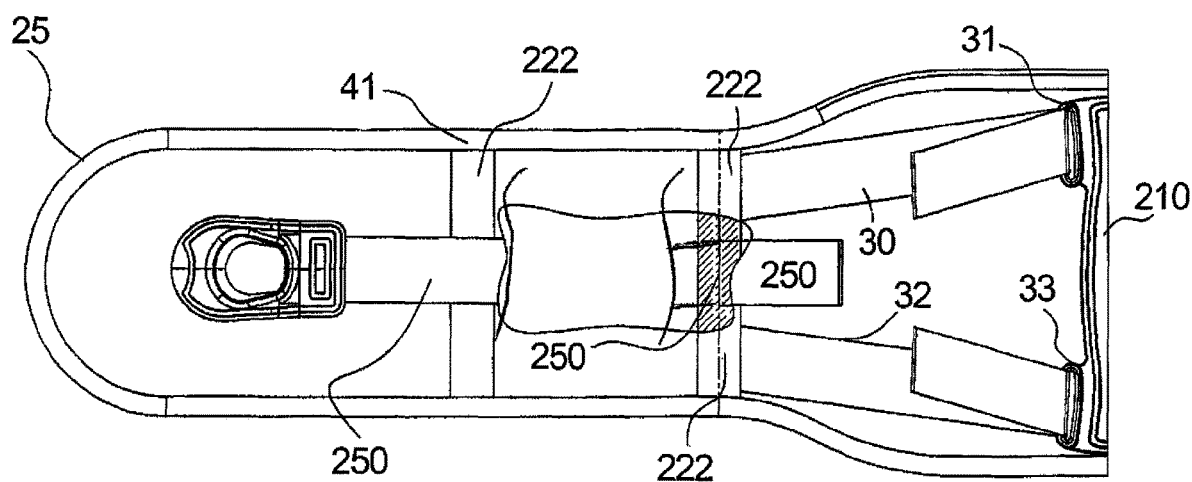
FIG. 9 is a view of FIG. 8 taken along the lines 9-9 to illustrate the support system under the center balance member system.

The center balance member system 230 has a proximal pivot support 232 and a distal pivot support 233. For this application, the terms "proximal" and "distal" are relative to the spine aligner 210. The proximal support 232 has an upper eyelet 234 and a lower eyelet 236 on its proximal end, a first pivot aperture 240 (see FIG. 7), an upper extension 242 (see FIG. 7) with an upper pivot, downwardly curvilinear guide aperture 244 (see FIGS. 5, 6, 7 and 10), a lower extension 246 (see FIG. 7) with a lower pivot, upwardly curvilinear guide aperture 248 (see FIGS. 5, 6, and 7); and a pull strap space 350 (see FIG. 7) positioned (a) between the upper extension 242 and the lower extension 246 that are designed to re-align, when necessary, pull-strap 250 and (b) distally spaced from the pivot aperture 240. The proximal support 232 tapers from the proximal end having a width d (400) toward the distal end having a width d-a (410) as illustrated at FIG. 7.

Upper trace 30 in the form a flexible tape, has (a) its left marginal end portion anchored, as by stitching, to the tension portion 222 on its proximal side (see FIGS. 5, 6, 9 and 10), (b) an intermediate portion passed through an upper spine eyelet 31 secured to the spine aligner 210 (see FIGS. 5, 6, 9, and 10), and (c) its other marginal end portion suitably affixed to the proximal support's 232 upper eyelet 234 (see FIGS. 5, 6, 7, 10). Similarly, lower trace 32 in the form a flexible tape, has (a) its left marginal end portion anchored, as by stitching, to the tension portion 222 on its proximal side (see FIGS. 5, 6, 8, 9 and 10), (b) an intermediate portion passed through a lower spine eyelet 33 secured to the spine aligner 210 (see FIGS. 5, 6, 8, 9 and 10), and (c) its other marginal end portion suitably affixed to the proximal support's 232 lower eyelet 236 (see FIGS. 5, 6, 7, 8, 10).

The distal pivot support 233 of the center balance member system 230 has a second pivot aperture 260 (see FIG. 7), an upper pivot aperture 262 (see FIG. 7), a lower pivot aperture 264 (see FIG. 7), a pull strap aperture 266 (see FIGS. 5-7, and 10), at least one flexible aperture 268 (see FIG. 7), and a pull strap retainer 270 (see FIGS. 5-8 and 10-11). The distal pivot support 233 essentially tapers (see FIG. 7) from its proximal end of width d-b (420) which is greater than width 410 and less than width 400 to its distal end of width d-c (430).

The proximal support's 232 first pivot aperture 240 aligns with the distal pivot support's 233 second pivot aperture 260; likewise the upper pivot, downwardly curvilinear guide aperture 244 aligns with the upper pivot aperture 262 and the lower pivot, upwardly curvilinear guide aperture 248 aligns with the lower pivot aperture 264. Once aligned, (a) first binder post and screw, rivet or equivalent thereof 280 (see FIGS. 5, 6, 8, and 10) is positioned at first pivot aperture 240 and second pivot aperture 260, (b) second binder post and screw, rivet or equivalent thereof 282 (see FIGS. 5, 6, and 10) is positioned the upper pivot, downwardly curvilinear guide aperture 244 and the upper pivot aperture 262, and (c) third binder post and screw, rivet or equivalent thereof 284 (see FIGS. 5,6, 8, and 10) is positioned the lower pivot, upwardly curvilinear guide aperture 248 and the lower pivot aperture 264. Collectively and individually each binder post and screw, rivet or equivalent thereof 280, 282, 284 pivotably secures the proximal support 232 and the distal pivot support 233 together.

A pull strip, generally indicated at 250 (see FIGS. 5, 6, 7-11), has a proximal end secured (a) to the tension portion 222 on its proximal side (see FIGS. 8 and 9) and (b) between the upper and lower traces 30, 32. The intermediate portion of the pull strip 250 is positioned at the pull strap space 350, through the pull strap aperture 266, and within the pull strap retainer 270. The pull strap's distal end is adapted to overlay the left band. The facing surfaces of the left band and the pull strip 250 may be provided with a suitable hook-and-loop fasteners such that the wearer need only grab the distal end of the pull strip, and pull it leftwardly, to selectively tighten the support system about his torso, and then reattach it to the band. The back and/or side panels may contain a pocket, such as indicated at 40, into which a stiffening insert, cold compress insert, a warm compress insert or combinations thereof 41 may be received.

Figure 10:
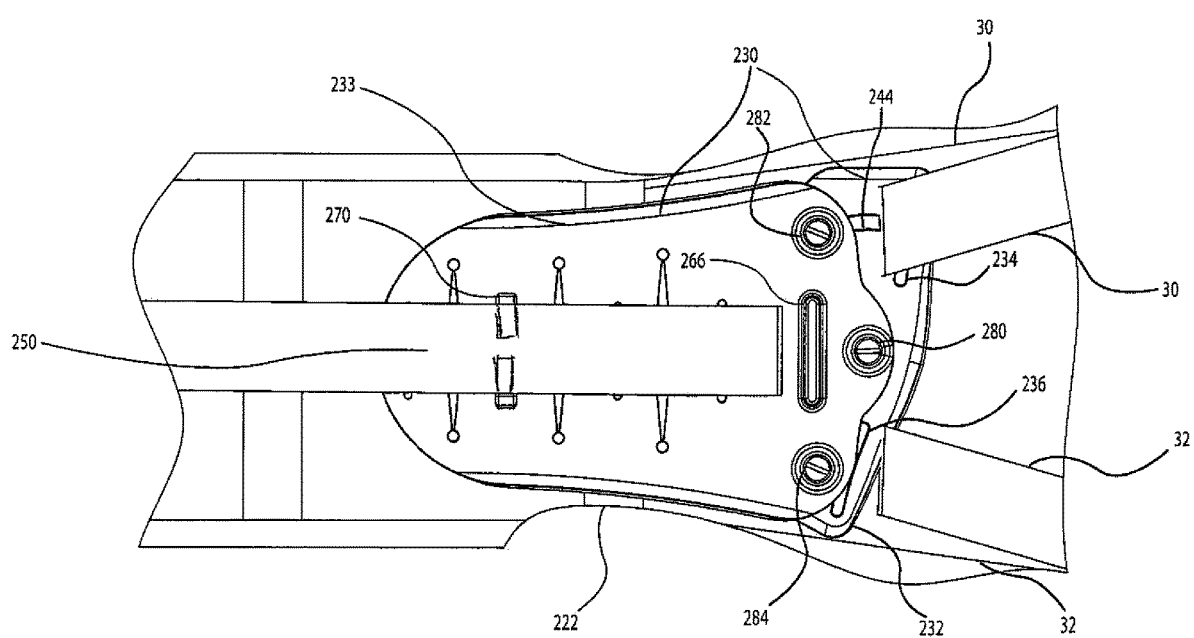
FIG. 10 is a view of FIG. 6 when the center balance member system is under stress from the traces and/or alignment member.

Assuming the support system is properly aligned and the patient has not altered the tension or support of the traces 30, 30', 32, 32' and/or alignment of the spine aligner 210, then the support system 20 should remain in its preferred natural state as illustrated at FIGS. 5, 6, 8 and 9. Due to, the support system's traces 30, 30', 32, 32' are sometimes under tension and/or the desired support is altered because the traces become unbalanced, or the spine aligner 210 is misaligned as illustrated FIG. 10 due to the patient's movements. When such unbalanced support system conditions, increased trace tension or altered support system conditions occur, the center balance member systems 230, 230' is designed to (a) permit the traces 30, 30', 32, 32' to temporally adjust by pivoting the proximal support 232 in order to accommodate the unbalanced support system conditions, increased trace tension or altered support system conditions as illustrated at FIG. 10 while the pull-strap 250 remains in the original desired position since the distal pivot support 233 continues to be properly aligned and positioned as illustrated at FIGS. 5, 6, 8, 9, and 10 when the proximal support 232 is pivoted; and (b) recoil the traces 30, 30', 32, 32' and spine aligner 210 toward the original desired equalization position of traces, the spine aligner, and the pull-strap 250 as illustrated at FIGS. 5, 6, 8 and 9.

The center balance member system 230 is designed to maximize its ability to adjust to the silhouette of the body—a fit person, while standing still, would normally have the proximal pivot support 232 top portion, relative to the bottom portion, closer to the person's spine while an obese person, while standing still, would normally have the proximal pivot support's bottom portion, relative to the top portion, closer to the person's spine to create the lowest possible profile and obtain a more proper and secure fit. In addition to adjusting to the silhouette of the body, the center balance member system 230 is designed to also adjust with the body through a rotational plane and a horizontal plane. In relation to the rotational plane, the center balance member system allows the patient's body to both bend up and down (for example, picking up a golf ball) and rotate side to side (for example, swinging a golf club) which permits, for example, the proximal pivot support 232 top portion adjust from being closer to the person's spine toward the proximal pivot support 232 bottom portion being closer to the person's spine (or vice versa) while the patient alters its rotational plane; and then being able to re-adjust to the low profiled, preferred standing still position. As for the horizontal plane; the traces 30, 32, and pull-strap 250 repositions the center balance member system 230 so the center balance member system 230, relative to the above-identified standing still position, is a greater distance, same distance or shorter distance from the patient's spine in response to the patient's diaphragm expanding or contracting while, for example, riding a lawn mower or a bus. It is preferred that this support system is applied to the following areas of the spine—the lumbar spine at L1 to L5 and/or the thoracic spine at T12 to T9.

Spinal Armor Embodiment

The spinal armor embodiment has a flexible spine aligner 400, as illustrated at FIGS. 12 and 13, with a vertebral arch configuration exterior surface 410 and a planar support interior surface 420. The planar support surface 420 attaches or removably attaches to the base portion 290. The vertebral arch configuration surface 410 has a plurality of cartilage-tongue elements 430 having a cartilage section 432 with a tongue section 434, a terminal cartilage element 436, and a plurality of flexible sections 438.

The planar support interior surface 420 has a superior end 422 having a first width W1, an inferior end 424 having a second width W2 which is greater than the first width W1; and right and left sides 426', 426 wherein each side 426, 426' has a plurality of eyelets 428, 428'. Each flexible section 438 has the eyelet 428, 428' extending distally from each side 426, 426'.

The flexible section 438 is positioned between (1) (a) the cartilage section 432 and a neighboring cartilage section 432 (identified as section 460) or (b) the terminal cartilage element 436 and a neighboring cartilage section (identified as section 462) and (2) the right side 426' and eyelet 428' and the left side 426 and eyelet 428. Between the right side 426' and eyelet 428' and the left side 426 and eyelet 428, the flexible section 438 is a convex surface (see, FIGS. 14, 15 and 17). Between the cartilage sections (and the terminal cartilage element 436 and a neighboring cartilage section), the flexible section 438 is a concave surface (see, FIGS. 16 and 17). Near each eyelet 428, 428' is a slight arch area 429, 429' that exposes a portion of a top surface of the planar support interior surface.

The concave-convex flexible section 438 has a center line 500; and each concave-convex section has a perpendicular center line 502. Along that center line 500, the concave-convex flexible section 438 has a first thickness of T1 (see, FIG. 16) under the cartilage section 432 and terminal cartilage element 436 and a second thickness of T2 (see, FIGS. 14, 15, and 16) which is less than T1. From the right side or left side 426', 426 toward the center line 500, the concave-convex flexible section 438 increases in thickness. Likewise, from the perpendicular center line 502 of each concave-convex flexible section 438 to the cartilage section 432 or terminal cartilage element 436, the concave-convex flexible section 438 increases in thickness. That way, the concave-convex flexible section 438 retains flexibility and sufficient stiffness to provide the desired support. The concave-convex flexible section 438 is made of polymeric material, for example and not limited to Nylon.

The cartilage section 432 and the terminal cartilage element 436, both of which are optional for the invention, are made of a softer, more cushionable polymeric material than the concave-convex flexible section 438 and is made of soft polymeric material for example thermoplastic polyurethane. Along the center line 500, the cartilage section 432 and the terminal cartilage element 436 are in the same plane as illustrated at FIGS. 12, 13, and 17. The cartilage section 432 and the terminal cartilage element 436 (A) have (a) side walls 472, wherein the side walls are perpendicular in relation to the concave-convex flexible section 438, (b) rounded tops 474, and (c) a box-like configuration; and (B) extend from the right side to the left side 426', 426. The tongue section 434 is positioned along the center line 500 and extends downward partially along the concave-convex flexible section 438, from the superior end 422 toward the inferior end 424 without crossing the perpendicular center line 502 of each concave-convex flexible section 438. Each tongue section 434 has (a) side walls 476, wherein the side walls are perpendicular in relation to the concave-convex flexible section 438, (b) rounded tops 478, and (c) a spade-like configuration.

The thicker sections of the concave-convex flexible section 438 are positioned below and in particular overlaid by the cartilage section 432, the terminal cartilage element 436, tongue section 434, are the more inflexible, stiffer sections of the flexible spine aligner 400 in order to provide the necessary stiffness for a support system 20. The cartilage section 432, the terminal cartilage element 436, tongue section 434 provide a cushioning effect to the patient wearing the support system 20 when the patient contacts a hard surface, like a chair, when wearing the support system 20.

Those side portions 23, 24, respectively, terminate in left and right marginal end portions 25, 26 and the marginal end portions 25, 26 are adapted to overlap one another in front of a wearer. These overlapped marginal end portions may be provided with various hook-and-loop fasteners, to secure the band about the torso of a wearer. Other types of fastening devices might be substituted for such hook-and-loop fasteners. Rear portion 22 and base portion 290 may be formed of an elastic material that will not gather, if desired. That elastic material may be an elastic polyurethane fabric, like Lycra™ brand fabric, and it has been determined that stretching the elastic material toward the marginal end portions permits adjustable platforms 890, 890' to a reset position, as illustrated at FIGS. 5 and 11.

As illustrated at FIG. 12, support system 20 is adapted to be worn by a person (not shown). The support system 20 is shown as including a closable band 21 adapted to encircle a wearer's torso. The band has a flexible spine aligner 400 adapted to be positioned proximate the spine of a wearer, a base portion 290, and has lateral side portions 23, 24 extending leftwardly and rightwardly, respectively, away from the rear portion 22. Positioned at or near the intersection between the rear portion 22 and (a) the lateral side portion 23 is a tension portion 222; and (b) the lateral side portion 24 is a tension portion 222'. Tension portions 222, 222' are, respectively, anchors for traces 30, 30'. The number of traces corresponds with the number eyelets 428, 428'—for each eyelet there is an equal number of traces. Each trace has (a) its marginal end portion anchored, as by stitching, to the tension portion 222 on its proximal side (see FIG. 12), (b) its intermediate portion passed through a respective eyelet 428, 428' secured to the flexible spine aligner 400, and (c) its other marginal end portion suitably affixed to a corresponding proximal eyelet 234 on the respective adjustable platform 890, 890'.

In the illustrated embodiment, the support system 20 is shown as having two adjustable platform 890, 890'. The left adjustable platform is generally indicated at 890, and the right adjustable platform is generally indicated at 890'. Inasmuch as these two adjustable platforms 890 are substantially identical, and are arranged as mirror images of one another, only the left adjustable platform 890 will be explicitly described. The reader will understand that the prime and same reference numeral will refer to the corresponding parts, portions or structure of right adjustable platform 890'.

For this application, the terms "proximal" and "distal" are relative to the spine aligner 210. The adjustable platform 890 has the plurality of proximal eyelets 234, a central eyelet 894, and a distal pull strap eyelet 892. The number of proximal eyelets 234 correspond with the number of traces 30 on each side. The central eyelet 894 receives a centralizing trace 896 that is on both left and right sides of the support system 20 and positioned under the flexible spine aligner 400 to inhibit the adjustable platforms 890 from being over adjusted.

The pull strip, generally indicated at 250 (see FIG. 12), has a proximal end secured to the distal pull strap eyelet 892. The pull strap's distal end is adapted to overlay the left band. The facing surfaces of the left band and the pull strip 250 may be provided with a suitable hook-and-loop fasteners 441 such that the wearer need only grab the distal end of the pull strip, and pull it leftwardly, to selectively tighten the support system about his torso, and then reattach it to the band. The back and/or side panels may contain a pocket, such as indicated at 40, into which a stiffening insert, cold compress insert, a warm compress insert or combinations thereof 41 may be received as described in the prior embodiment of the present invention.

The adjustable platform 890 is designed to maximize its ability to adjust to the silhouette of the body—a fit person, while standing still, would normally have the adjustable platform's top portion, relative to the bottom portion, closer to the person's spine while an obese person, while standing still, would normally have the adjustable platform's bottom portion, relative to the top portion, closer to the person's spine to create the lowest possible profile and obtain a more proper and secure fit. In addition to adjusting to the silhouette of the body, the adjustable platform 890 is designed to also adjust with the body through a rotational plane and a horizontal plane. In relation to the rotational plane, the adjustable platform allows the patient's body to both bend up and down (for example, picking up a golf ball) and rotate side to side (for example, swinging a golf club) which permits, for example, the adjustable platform 890 top portion adjust from being closer to the person's spine toward the adjustable platform 890 bottom portion being closer to the person's spine (or vice versa) while the patient alters its rotational plane; and then being able to re-adjust to the low profiled, preferred standing still position. As for the horizontal plane; the traces 30 and pull-strap 250 repositions the adjustable platform 890 so the adjustable platform 890, relative to the above-identified standing still position, is a greater distance, same distance or shorter distance from the patient's spine in response to the patient's diaphragm expanding or contracting while, for example, riding a lawn mower or a bus. It is preferred that this support system is applied to the following areas of the spine—the lumbar spine at L1 to L5 and/or the thoracic spine at T12 to T9.

Therefore, while the preferred embodiment of the improved equalizing back support system has been shown and described, and several modifications thereof discussed, persons skilled in this art will readily appreciate that various additional changes and modifications may be made, without departing from the spirit of the invention, as defined and differentiated by the following claims.

The invention claimed is:

1. A back support system adapted to be worn by a person, comprising:

a single, unitary band adapted to encircle at least a portion of wearer's torso and wherein the single, unitary band covers the entire encircled torso portion, said single, unitary band has
- (a) a rear portion section adapted to be positioned proximate the spine of a wearer, and
- (b) a first side portion section and a second side portion section, the first and second side portions extend (i) from and (ii) away from said rear portion in opposite directions, and each of the first and second side portions has a marginal end portion, each marginal end portion is adapted to overlap one another proximate the front of such wearer, each marginal end portion is adapted to be selectively secured to one another such that said band encircles a wearer's torso; and a tightening mechanism mounted on said single, unitary band, said tightening mechanism having a spine aligner adapted to be positioned along the spine of the wearer and a first pivot adjusting balance member system on the first side portion section and a second pivot adjusting balance member system on the second side portion section, the first and second pivot adjusting balance systems are independent of each other since each pivot adjusting balance system has a proximal pivot support unit, a distal pivot support unit, an upper trace, a lower trace, and a pull-strap;

(A) the proximal pivot support unit has
- (i) an upper eyelet on its proximal end;
- (ii) a lower eyelet on its proximal end,
- (iii) a first pivot aperture,
- (iv) an upper extension with an upper pivot, downwardly curvilinear guide aperture,
- (v) a lower extension with a lower pivot, upwardly curvilinear guide aperture, and
- (vi) a pull strap space positioned (a) between the upper extension and the lower extension and (b) distally spaced from the first pivot aperture;

(B) the distal pivot support unit has
- (i) a second pivot aperture,
- (ii) an upper pivot aperture,
- (iii) a lower pivot aperture,
- (iv) a pull strap aperture,
- (v) at least one flexible aperture, and
- (vi) a pull strap retainer;

(C) the proximal pivot support unit and the distal pivot support unit are pivotally mounted on each other such that:
- (A.i) the first pivot aperture aligns with the second pivot aperture,
- (A.ii) the upper pivot, downwardly curvilinear guide aperture aligns with the upper pivot aperture, and
- (A.iii) the lower pivot, upwardly curvilinear guide aperture aligns with the lower pivot aperture; and
- (B.i) a first fastener secures the first pivot aperture to the second pivot aperture, (B.ii) a second fastener secures the upper pivot, downwardly curvilinear guide aperture to the upper pivot aperture, and
(B.iii) a third fastener secures the lower pivot, upwardly curvilinear guide aperture to the lower pivot aperture;
(D) the upper trace secured to a respective first or second side portion section and engaging an upper marginal end portion of the spine aligner and the upper eyelet of the proximal pivot support unit,
(E) the lower trace secured to the respective first or second side portion section and engaging a lower marginal end portion of the spine aligner and the lower eyelet of the proximal pivot support unit,
(F) the pull-strap, said pull-strap having one marginal end portion secured to the respective first or second side portion section, and having an intermediate portion passed through the pull strap space and the pull strap aperture, said pull-strap being adapted to be secured to the respective first or second side portion section at any of a plurality of positions relative thereto; whereby said pull-strap may be grasped, pulled away from said rear portion and secured to said single, unitary band to selectively tighten said single, unitary band about said wearer's torso.

2. The back support system as set forth in claim 1 wherein said rear portion is formed of an elastic material.

3. The back support system as set forth in claim 1 wherein said rear portion is provided with a pocket, and further comprising an insert adapted to be received in said pocket.

4. The back support system as set forth in claim 1 wherein when said pull-strap is tightened, substantially equal tensile forces will be exerted on said upper and lower traces.

5. The back support system as set forth in claim 4 wherein said pivot adjusting balance member system is mounted for movement such that when said pull-strap is tightened, substantially equal tensile forces will be exerted on said upper and lower traces independent of the position of said wearer's torso.

6. The back support system as set forth in claim 1 wherein said spine aligner is a flexible spine aligner, the flexible spine aligner has
(a) a planar support interior surface adapted to contact the single, unitary band,
(b) a superior end having a first width,
(c) an inferior end having a second width which is greater than the first width,
(d) a centerline that extends from the superior end to the inferior end of the flexible spine aligner,
(e) a left side,
(f) a right side,
(g) a plurality of eyelet pair sets, each eyelet pair set has a first eyelet extending outwardly from the left side and a second eyelet extending outwardly from the right side,
(h) a flexible section of a vertebral arch configuration exterior surface contains one eyelet pair set, each flexible section has
a convex polymeric surface between the right and left sides,
a flexible section superior end;
a flexible section inferior end;
a concave polymeric surface that extends from the flexible section superior end to the flexible section inferior end,
along the centerline of each flexible section, the flexible section has a superior high point at the flexible section superior end and
an inferior high point at the flexible section inferior end wherein the superior high point and the inferior high point are the two highest points on each flexible section relative to the planar support interior surface in each flexible section.

7. The back support system as set forth in claim 1 and further comprising a hook and loop fastener operatively interposed between said pull-strap and said respective first or second side portion section for releasably holding said pull-strap to said respective first or second side portion section.

8. The back support system as set forth in claim 1 wherein one of said tightening mechanisms is mounted on each of said side portions.

9. The back support system as set forth in claim 1 wherein each of said upper trace and lower trace has one end fixed to the respective first or second side portion section, has an intermediate portion passed through an eyelet arranged proximate said rear portion, and has another end engaging an associated end of said pivot adjusting balance member system.

10. The back support system as set forth in claim 1 wherein said pull-strap has one end secured to the respective first or second side portion section, has an intermediate portion passed through an eyelet arranged between said upper and lower marginal end portions, and has another end adapted to overlie another portion of said side portion.

11. A back support system adapted to be worn by a person, comprising:
a single, unitary band adapted to encircle a wearer's torso, said single, unitary band has (a) a rear portion section adapted to be positioned proximate the spine of a wearer, and (b) a first side portion section and a second side portion section, the first and second side portions extend (i) from and (ii) away from said rear portion in opposite directions, and each of the first and second side portions has a marginal end portion, each marginal end portion is adapted to overlap one another proximate the front of such wearer, each marginal end portion is adapted to be selectively secured to one another such that said band encircles a wearer's torso; and
a tightening mechanism mounted on said band, said tightening mechanism having a flexible spine aligner adapted to be positioned along the spine of the wearer and a first pivot adjusting balance member system on the first side portion section and a second pivot adjusting balance member system on the second side portion section;
the flexible spine aligner has
(a) a planar support interior surface adapted to contact the band,
(b) a superior end having a first width,
(c) an inferior end having a second width which is greater than the first width,
(d) a centerline that extends from the superior end to the inferior end of the flexible spine aligner,
(e) a left side,
(f) a right side,
(g) a plurality of eyelet pair sets, each eyelet pair set has a first eyelet extending outwardly from the left side and a second eyelet extending outwardly from the right side,
(h) a flexible section of a vertebral arch configuration exterior surface contains one eyelet pair set, each flexible section has a convex polymeric surface between the right and left sides, a concave polymeric surface that extends from the flexible section's superior end to the flexible section's inferior end, along the centerline of each flexible section, the flexible section has a superior high point at the flexible section superior end and an inferior high point at the flexible section inferior end wherein the superior high point and the inferior high point are the two highest points on each flexible section relative to the planar support interior surface in each flexible section;

the first and second pivot adjusting balance systems are independent of each other since each pivot adjusting balance system has a proximal pivot support unit, a distal pivot support unit, an upper trace, a lower trace, and a pull-strap;

(A) the proximal pivot support unit has
  (i) an upper eyelet on its proximal end;
  (ii) a lower eyelet on its proximal end,
  (iii) a first pivot aperture,
  (iv) an upper extension with an upper pivot, downwardly curvilinear guide aperture, (v) a lower extension with a lower pivot, upwardly curvilinear guide aperture, and
  (vi) a pull strap space positioned (a) between the upper extension and the lower extension and (b) distally spaced from the first pivot aperture;
(B) the distal pivot support unit has
  (i) a second pivot aperture,
  (ii) an upper pivot aperture,
  (iii) a lower pivot aperture,
  (iv) a pull strap aperture,
  (v) at least one flexible aperture, and
  (vi) a pull strap retainer;
(C) the proximal pivot support unit and the distal pivot support unit are pivotally mounted on each other such that:
  (A.i) the first pivot aperture aligns with the second pivot aperture,
  (A.ii) the upper pivot, downwardly curvilinear guide aperture aligns with the upper pivot aperture, and
  (A.iii) the lower pivot, upwardly curvilinear guide aperture aligns with the lower pivot aperture; and
  (B.i) a first fastener secures the first pivot aperture to the second pivot aperture,
  (B.ii) a second fastener secures the upper pivot, downwardly curvilinear guide aperture to the upper pivot aperture, and
  (B.iii) a third fastener secures the lower pivot, upwardly curvilinear guide aperture to the lower pivot aperture;
(D) the upper trace secured to a respective first or second side portion section and engaging an upper marginal end portion of the spine aligner and the upper eyelet of the proximal pivot support unit,
(E) the lower trace secured to the respective first or second side portion section and engaging a lower marginal end portion of the spine aligner and the lower eyelet of the proximal pivot support unit,
(F) the pull-strap, said pull-strap having one marginal end portion secured to the respective first or second side portion section, and having an intermediate portion passed through the pull strap space and the pull strap aperture, said pull-strap being adapted to be secured to the respective first or second side portion section at any of a plurality of positions relative thereto; whereby said pull-strap may be grasped, pulled away from said rear portion and secured to said single, unitary band to selectivelytighten said single, unitary band about said wearer's torso.

12. The back support system as set forth in claim 11 wherein said rear portion is formed of an elastic material.

13. The back support system as set forth in claim 11 wherein said rear portion is provided with a pocket, and further comprising an insert adapted to be received in said pocket.

14. The back support system as set forth in claim 11 wherein when said pull strap is tightened, substantially equal tensile forces will be exerted on said upper and lower traces.

15. The back support system as set forth in claim 14 wherein said pivot adjustable balance member system is mounted for movement such that when said pull-strap is tightened, substantially equal tensile forces will be exerted on said upper and lower traces independent of the position of said wearer's torso.

16. The back support system as set forth in claim 11 and further comprising a hook and loop fastener operatively interposed between said pull-strap and said respective first or second side portion section for releasably holding said pull-strap to said respective first or second side portion section.

17. The back support system as set forth in claim 11 wherein one of said tightening mechanisms is mounted on each of said side portions.

18. The back support system as set forth in claim 11 wherein each of said traces has one end fixed to the respective first or second side portion section, has an intermediate portion passed through an eyelet arranged proximate said rear portion, and has another end engaging an associated end of said pivot adjusting balance member system.

19. The back support system as set forth in claim 11 wherein said pull-strap has one end secured to the respective first or second side portion section, has an intermediate portion passed through an eyelet arranged between said upper and lower marginal end portions, and has another end adapted to overlie another portion of said side portion.

* * * * *